(12) United States Patent
Kang

(10) Patent No.: US 12,070,600 B2
(45) Date of Patent: Aug. 27, 2024

(54) METHOD FOR HIGH FREQUENCY PULSE APPLICATION FOR COSMETIC IMPROVEMENT EFFECT OF SKIN AND SKIN CARE DEVICE USING THE SAME

(71) Applicant: SHENB Co., Ltd., Seoul (KR)

(72) Inventor: Sun Young Kang, Seoul (KR)

(73) Assignee: SHENB CO., LTD., Seoul (KR)

( * ) Notice: Subject to any disclaimer, the term of this patent is extended or adjusted under 35 U.S.C. 154(b) by 0 days.

(21) Appl. No.: 18/517,889

(22) Filed: Nov. 22, 2023

(65) Prior Publication Data

US 2024/0173545 A1    May 30, 2024

(30) Foreign Application Priority Data

Nov. 24, 2022   (KR) .................. 10-2022-0159311

(51) Int. Cl.
  *A61B 18/14*   (2006.01)
  *A61N 1/00*    (2006.01)
  *A61N 1/32*    (2006.01)

(52) U.S. Cl.
  CPC .............. *A61N 1/328* (2013.01); *A61N 1/325* (2013.01); *A61N 1/327* (2013.01)

(58) Field of Classification Search
  CPC ................ A61B 18/1206; A61B 18/14; A61B 2018/00452; A61B 2018/00458;
  (Continued)

(56) References Cited

U.S. PATENT DOCUMENTS 4,727,874 A * 3/1988 Bowers ..................... H03F 1/52
                                          330/251
7,303,557 B2 * 12/2007 Wham ............... A61B 18/1442
                                          606/42

(Continued)

FOREIGN PATENT DOCUMENTS

KR   10-2010-0082140 A    7/2010
KR     10-1401133 B1      6/2014

(Continued)

OTHER PUBLICATIONS

International search report issued on Feb. 26, 2024, in counterpart International Patent Application No. PCT/KR2023/018819 (4 pages).

*Primary Examiner* — Michael F Peffley
(74) *Attorney, Agent, or Firm* — NSIP Law

(57) ABSTRACT

The present disclosure relates to a skin care method based on high-frequency pulses application, comprising: generating high frequency pulses and applying the high-frequency pulses to the skin, wherein said generating and applying the high-frequency pulses includes outputting high frequency (RF) for a certain period of time to the skin, the high frequency (RF) output for the certain period of time has a selected number of pulses in the range of 1 to N, when the selected number of pulses is any one of 2 to N, each pulse has On time and Off time, the On time is a time period when pulse waveform is output, and the Off time is a time period when no pulse waveform is output, and the On time and the Off time are alternately repeated based on the number of pulses during the certain period of time for outputting high frequency (RF).

12 Claims, 16 Drawing Sheets

(58) Field of Classification Search
CPC .. A61B 2018/00464; A61B 2018/0047; A61B 2018/00577; A61B 2018/00702; A61B 2018/00708; A61B 2018/00732; A61B 2018/0072; A61B 2018/00761; A61B 2018/00738; A61N 1/325; A61N 1/327; A61N 1/328
See application file for complete search history.

(56) References Cited

U.S. PATENT DOCUMENTS

| | | | |
|---|---|---|---|
| 8,221,411 B2* | 7/2012 | Francischelli | A61B 18/1492 606/41 |
| 9,522,039 B2* | 12/2016 | Behnke | A61B 18/1206 |
| 9,770,283 B2* | 9/2017 | Gilbert | A61B 18/1206 |
| 2019/0255321 A1* | 8/2019 | Planard-Luong | H03K 7/02 |

FOREIGN PATENT DOCUMENTS

| | | |
|---|---|---|
| KR | 10-2019-0049773 A | 5/2019 |
| KR | 10-2119517 B1 | 6/2020 |
| KR | 10-2022-0137190 A | 10/2022 |
| KR | 10-2538213 B1 | 6/2023 |

* cited by examiner

METHOD FOR HIGH FREQUENCY PULSE APPLICATION FOR COSMETIC IMPROVEMENT EFFECT OF SKIN AND SKIN CARE DEVICE USING THE SAME

CROSS-REFERENCE TO RELATED APPLICATIONS

This application claims priority to Korean Patent Application No. 10-2022-0159311, filed on Nov. 24, 2022, the entire contents of which are incorporated herein by reference.

TECHNICAL FIELD

The present disclosure relates to a method of applying a high-frequency pulse to the skin for skin care and a device for skin care using the same, and, more particularly, to a method of applying a high-frequency pulse to the skin for skin care and a device for skin care using the same, where the cycle and the energy of high-frequency pulses applied to the skin can be carefully controlled by a user based on the purposes of skin care or skin treatment as well as the conditions of the skin.

BACKGROUND

As one of skin care devices, a device applying high-frequency pulses to the skin has been broadly used. However, the conventional high-frequency application device for skin care applies only one preset type of pulses to the skin.

For example, as shown in FIG. 1, the conventional skin care device applies pulses to the skin for a certain period of time, such as 800 ms (i.e., pulse ON), and does not apply pulses for a certain period of time thereafter (i.e., pulse OFF). The pulse application to the skin is performed by repeating such a process.

In addition, there is conventional skin care devices which allow users to select the number of pulses to be applied to the skin.

However, such devices merely repeat an application of a preset type of pulses to the skin for the user-selected number of times.

For example, assuming that a user sets the number of pulses to "5," they simply repeat an application of one type of pulse shown in FIG. 1, five times in succession.

As such, in the case of the conventional devices for skin care, a type of pulses to be applied is set in advance and only the preset type of pulses are applied. Accordingly, an adjustment of a pulse type based on the purpose of skin care or skin treatment as well as the conditions of a user's skin is not possible at all.

The conventional skin care devices, which output only one type of pulses, have a problem that an extremely precise control of the devices is required in order to apply a desired amount of energy to the skin by using one type pulse, and thus, it was difficult to bring about a remarkable effect on skin care with the conventional devices.

In addition, the above-described conventional device for skin care can apply a preset type of frequency pulses for an increased number of times based on the selection of pulse number. Such an operation artificially increases the time of outputting high frequencies (total RF time), therefore, causes an excessive coagulation of tissue in the skin, which results in a patient's pain due to prolonged exposure to high frequency, skin fatigue, or side effects on the skin due to excessive treatment.

PRIOR ART DOCUMENTS

Patent Documents

Patent Document 1: Korean Laid-open Patent Publication No. 10-1413552
Patent Document 2: Korean Laid-open Patent Publication No. 10-2119517

SUMMARY

The present disclosure has been made in an effort to provide a method of applying a high-frequency pulse to the skin for skin care and a device for skin care using the same, where it carefully controls the cycle and the energy of high-frequency pulses applied to the skin based on the purpose of skin care or skin treatment as well as the conditions of the skin and allows a user to arbitrarily control high frequency pulses applied to the skin.

The present disclosure has been made in an effort to provide a method of applying a high-frequency pulse to the skin for skin care and a device for skin care using the same, where the Off time can be automatically set longer than the On time when the selected number of high frequency pulses applied to the skin is increased, so that the time for outputting high frequency (RF) is increased in a safer manner, and thereby delivering high frequency evenly into the skin layer for a relatively long time and improving safety in the high frequency (RF) application to the skin.

The present disclosure has been made in an effort to provide a method of applying a high-frequency pulse to the skin for skin care and a device for skin care using the same, where it stably applies high-frequency pulses to the entire skin layer from the shallow layer to the deep layer and delivers them evenly into tissue in the skin.

The present disclosure has been made in an effort to provide a method of applying a high-frequency pulse to the skin for skin care and a device for skin care using the same, where it controls and treats the aspects of the skin's coagulative necrotic reaction, non-necrotic coagulation reaction, and non-necrotic thermal reaction by using the enhanced method of applying high-frequency pulses to the skin.

The present disclosure has been made in an effort to provide a method of applying a high-frequency pulse to the skin for skin care and a device for skin care using the same, where it secures cosmetic improvements of the skin, including removal of hair of various colors, by using the enhanced method of applying high-frequency pulses to the skin.

The present disclosure provides a method of generating high-frequency pulses and applying them to the skin for skin care,
  wherein said generating the high-frequency pulses and applying the high-frequency pulses includes outputting high frequency (RF) for a certain period of time to the skin,
  the high frequency (RF) output for the certain period of time has a selected number of pulses in the range of 1 to N (N is a natural number),
  when the selected number of pulses is any one of 2 to N, each pulse, has On time and Off time, the On time is a time period when pulse waveform is output, and the Off time is a time period when no pulse waveform is output, and
  the On time and the Off time are alternately repeated based on the number of pulses during the certain period of time for outputting high frequency (RF), so that a desired high-frequency pulse is applied to the skin during the On time.

The time for outputting high frequency (RF) may be in the range of 100 ms to 7,000 ms, the frequency of the high frequency (RF) may be in the range of 0.5 MHz to 2 MHz, and the energy of the high frequency (RF) may be in the range of 0.0025 J to 192 J.

The Off time may be automatically set longer than the On time when the selected number of high frequency pulses applied to the skin is increased, so that the time for outputting high frequency (RF) is increased in a safer manner, and thereby delivering high frequency evenly into the skin layer for a long time and improving safety in applying the high frequency to the skin.

When the selected number of pulses is any one of 2 to N, the time period of the On time is determined by Equation 1 and the time period of the Off time is determined by Equation 2.

$$\text{On time} = [T_{RF\ Time} \times \{(10-\text{Pulse}+1) \times 10\} \div 100] \div \text{Pulse} \quad \text{(Equation 1)}$$

$$\text{Off time} = [T_{RF\ Time} \times \{(\text{Pulse}-1) \times 10\} \div 100] \div \text{Pulse}, \quad \text{(Equation 2)}$$

wherein the $T_{RF\ Time}$ denotes the time for outputting high frequency (RF), and the Pulse denotes the number (natural number) of high frequency pulses.

The time period for outputting the high frequency (RF), the frequency of the high frequency and the energy of the high frequency are respectively adjustable.

The present disclosure provides a device for skin care that generates high-frequency pulses and applies them to the skin, including a main body and a handpiece connected to the main body to apply high-frequency pulses to the skin,
wherein the main body may include a power supply unit for supplying power to the device, a high-frequency signal generator for generating a high-frequency pulse signal applied to the skin, an adjustment unit for determining an adjustment of an output of high frequency signal generator, and a controller for controlling the overall operation of the device as well as the output of high-frequency pulses in response to the adjustment determined by the adjustment unit,
the adjustment unit may include a high frequency output time adjusting unit for determining an adjustment of a time period for outputting high frequency (RF) to be applied to the skin; a high frequency pulse number adjusting unit for determining an adjustment of the number of pulses in the range of 1 to N (N is a natural number); a high frequency output intensity adjusting unit for determining an adjustment of the intensity of the output of high-frequency (RF); a high-frequency frequency adjusting unit for determining an adjustment of a high-frequency (RF) frequency; a high frequency pulse width adjusting unit for determining an adjustment of the width of a high frequency (RF) pulse; a needle length adjusting unit for determining an adjustment of a length of a needle to be inserted into the skin, the needle being mounted on the handpiece; and a high-frequency waveform output unit for determining a pulse waveform according to the adjustment determined by the high frequency output time adjusting unit and the high frequency pulse number adjusting unit.

In order to apply a desired high frequency pulse to the skin during the On time, by the high-frequency waveform output unit, each pulse of the pulse waveform has On time and Off time, the On time is a time period when pulse waveform is output, and the Off time is a time period when no pulse waveform is output; when the selected number of pulses is 1, a time period of the On time is identical with the time period for outputting high frequency (RF), and Off time follows after the On time, and when the selected number of pulses is any one of 2 to N, the On time and the Off time are alternately repeated based on the number of pulses during the time period for outputting high frequency (RF).

The handpiece may include an electrode unit that receives a high-frequency pulse signal generated by the high-frequency signal generator and applies it to the skin.

The electrode unit may include a plurality of electrodes.

The plurality of electrodes may include needles.

The time for outputting high frequency (RF) may be in the range of 100 ms to 7,000 ms, the frequency of the high frequency (RF) may be in the range of 0.5 MHz to 2 MHz, and the energy of the high frequency (RF) may be in the range of 0.0025 J to 192 J.

The high-frequency waveform output unit may be programmed to automatically set the Off time longer than the On time when the selected number of high frequency pulses applied to the skin is increased, so that the time for outputting high frequency (RF) is increased in a safer manner, and thereby delivering high frequency evenly into the skin layer for a relatively long time and improving safety in the high frequency application to the skin.

When the selected number of pulses is any one of 2 to N, the time period of the On time is determined by Equation 1 and the time period of the Off time is determined by Equation 2).

$$\text{On time} = [T_{RF\ Time} \times \{(10-\text{Pulse}+1) \times 10\} \div 100] \div \text{Pulse} \quad \text{(Equation 1)}$$

$$\text{Off time} = [T_{RF\ Time} \times \{(\text{Pulse}-1) \times 10\} \div 100] \div \text{Pulse}, \quad \text{(Equation 2)}$$

wherein the $T_{RF\ Time}$ denotes the time for outputting high frequency (RF), and the Pulse denotes the number (natural number) of high frequency pulses.

The time period for the On time and the Off time is adjustable by using the adjustment unit.

A plurality of types of handpieces are attachable to the main body and they can be interchanged with each other, and wherein a type of the handpiece to be used can be designated by using the adjustment unit.

According to the present disclosure, it may be possible to carefully control the cycle and the energy of high-frequency pulses applied to the skin based on the purpose of skin care or skin treatment as well as the conditions of the skin and for a user to arbitrarily control high frequency pulses applied to the skin, thereby enhancing effect on skin care and convenience in use. In particular, according to the present disclosure, the Off time may be automatically set longer than the On time when the selected number of high frequency pulses applied to the skin is increased, so that the time for outputting high frequency (RF) is increased in a safer manner, and delivering high frequency evenly into the skin layer for a relatively long time and improving safety in the high frequency (RF) application to the skin.

According to the present disclosure, it may be possible to resolve the problems of the conventional method: excessive coagulation of tissue in the skin, a patient feeling pain due to prolonged exposure to high frequency, skin fatigue, side effects on the skin due to excessive treatment, etc.

According to the present disclosure, it may be possible to stably apply high-frequency pulses to the entire skin layer from the shallow layer to the deep layer and deliver them evenly into tissue in the skin, thereby enhancing the effects on skin care.

According to the present disclosure, it may be possible to control and treat the aspects of the skin's coagulative necrotic reaction, non-necrotic coagulation reaction, and non-necrotic thermal reaction by enhancing the method of applying high-frequency pulses to the skin.

According to the present disclosure, it may be possible to secure cosmetic improvement of the skin, including removal of hair of various colors, by using the enhanced method of applying high-frequency pulses to the skin.

DETAILED DESCRIPTION

The desirable embodiments of the present disclosure can be described with reference to the attached drawings as follows. Through this detailed description, the purpose, the components, and the features of the present disclosure will be better understood.

FIGS. 2 to 12E are figures for a better understanding of a method for applying a high-frequency pulse to the skin for skin care and a device for skin care using the same according to the present disclosure.

A device 100 for skin care according to an embodiment of the present disclosure may be a device that generates high-frequency pulses and applies them to the skin for use in cosmetic improvement and treatment of the skin, and is configured to perform a method of applying a high-frequency pulse to the skin in order to cosmetically improve the skin.

Figure 7:
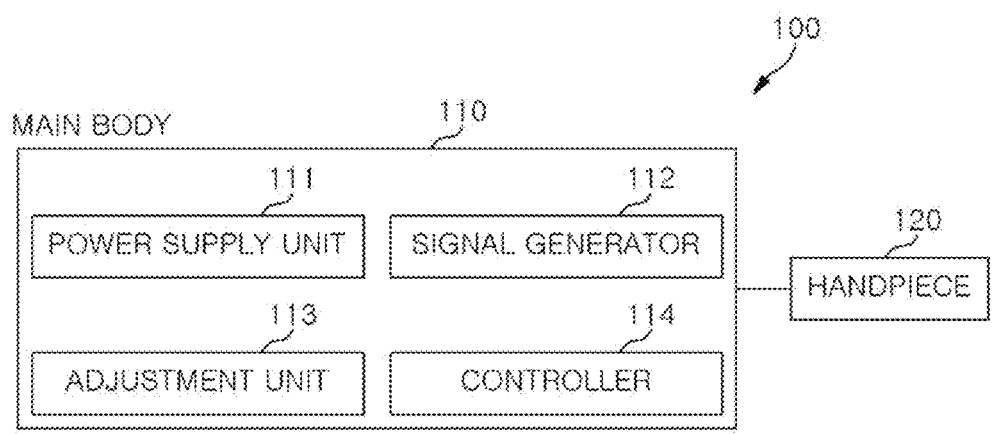
FIG. 7 is a block diagram showing a device for skin care according to the present disclosure.
Figure 8:
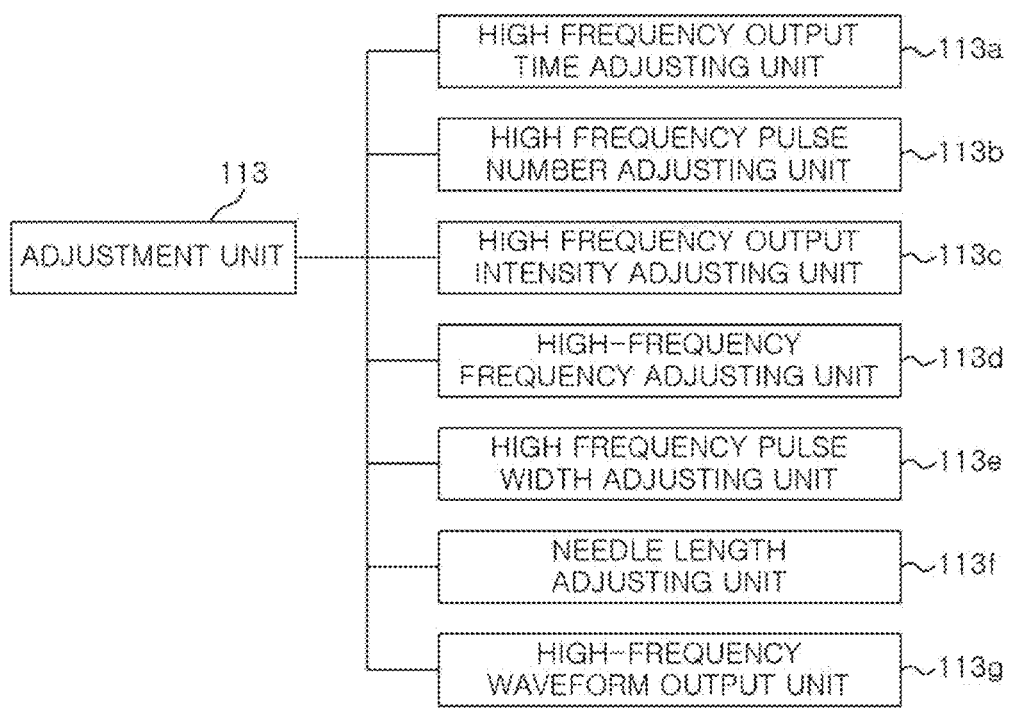
FIG. 8 is a block diagram showing an adjustment unit of the device for skin care according to the present disclosure.
Figure 9:
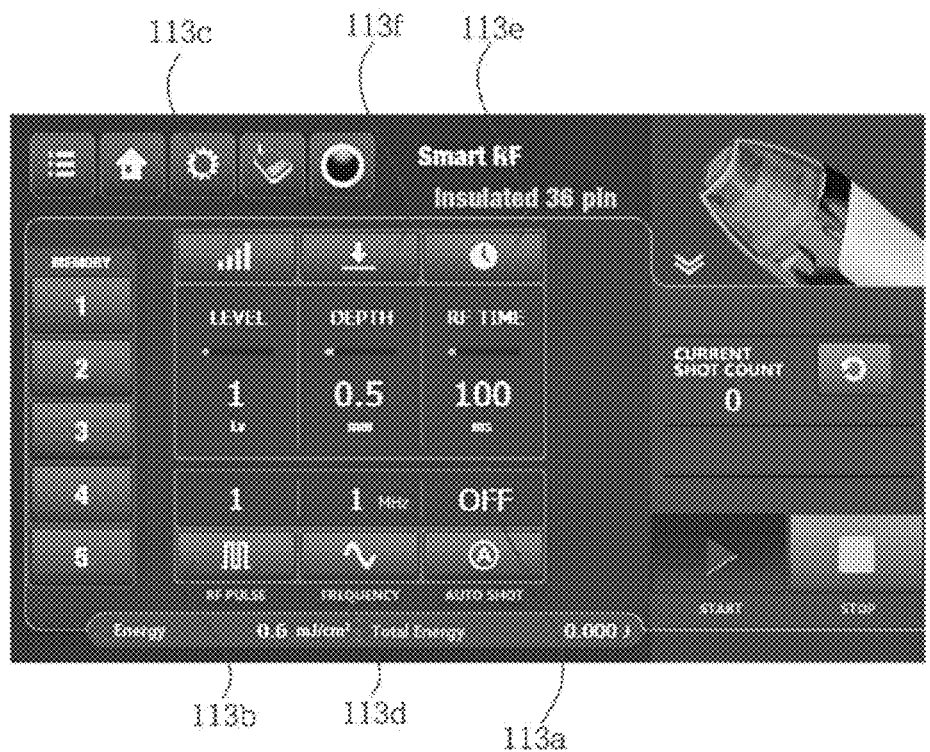
FIG. 9 is a view of a screen of the adjustment unit of the device for skin care according to the present disclosure.

As shown in FIGS. 7 to 9, the device 100 for skin care according to an embodiment of the present disclosure may include a main body 110 and a handpiece 120 connected to the main body 110 and used to apply a high-frequency pulse to the skin.

Preferably, the main body 110 can be movable.

The main body 110 may include a power supply unit 111 for supplying power to the device, a high-frequency signal generator 112 for generating a signal of a high-frequency pulse applied to the skin, an adjustment unit 113 for adjusting the output of the high-frequency pulse applied to the skin, and a controller 114 for controlling the overall operation of the device as well as the output of a high-frequency pulse in response to the adjustment by the adjustment unit.

It may be desirable the adjustment unit 113 be provided in the form of a touch screen, and the adjustment unit 113 may also display the overall status of the device with operation settings and the like.

The adjustment unit 113 may include a high frequency output time adjusting unit 113a for selecting and adjusting the time period for outputting high frequency (RF) to be applied to the skin, a high frequency pulse number adjusting unit 113b for selecting and adjusting the number of pulses in the range of 1 pulse to N pulses (N is a natural number) to be applied during the time period of the high frequency (RF) output, a high frequency output intensity adjusting unit 113c for selecting and adjusting the intensity of high frequency (RF) output, a high-frequency frequency adjusting unit 113d for selecting and adjusting a high-frequency (RF) frequency, a high frequency pulse width adjusting unit 113e for selecting and adjusting the width of a high frequency (RF) pulse to be applied, a needle length adjusting unit 113f for selecting and adjusting the length of a needle to be inserted into the skin, the needle being mounted on the handpiece 120, and a high-frequency waveform output unit 113g generating an output of pulses according to adjustment by the high frequency output time adjusting unit and the high frequency pulse number adjusting unit by using a software program.

When the 1-pulse option is selected, the high-frequency waveform output unit 113g causes the device to have an Off time where no pulse waveform is output after an On time where pulse waveform is output, during the time period for outputting high frequency (RF).

In addition, when the number of pulses in the range of 2 to N (N is a natural number), excluding 1 pulse, is selected, the high-frequency waveform output unit 113g cause the device to have the On time where pulse waveform is output and after the Off time where no pulse waveform is output, and, based on the selection for the number of pulses, the On time and the Off time may be alternately repeated, during the time period for outputting high frequency (RF).

In this case, y a desired high-frequency pulse can be applied to the skin during the On time.

Here, the On time and the Off time may be adjusted via the adjustment unit 113.

Here, the time for outputting high frequency (RF), the high-frequency frequency, and the high-frequency energy may be adjusted, respectively.

In detail, by the adjustment unit 113, the time period for outputting high frequency (RF) may be selected in the range of 100 ms to 7,000 ms, the frequency of high frequency (RF) may be selected in the range of 0.5 MHz to 2 MHz, and the energy of the high frequency (RF) may be selected in the range of 0.0025 J to 192 J.

In this case, if the energy of the high frequency (RF) is lowered to less than 0.0025 J, the high frequency may not be sufficiently applied to the skin, so that desired effects of the present disclosure, including cosmetic improvement of the skin, may not be sufficiently obtained. When the energy of the high frequency (RF) exceeds 192 J, damage to the skin may occur.

Figure 6:
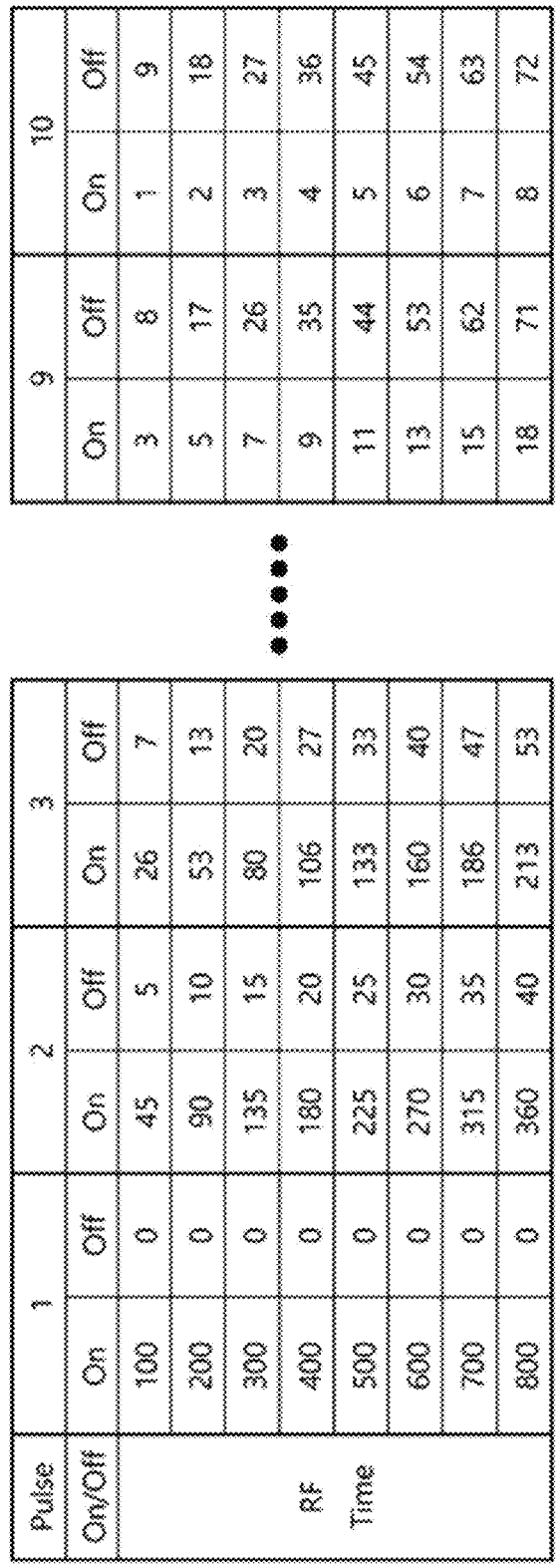
FIG. 6 is a data table showing an example of the variations of the On time and the Off time pairs depending on the number of high frequency pulses according to the present disclosure.

FIG. 6 is a data table showing an example of the variations of the On time and the Off time pairs depending on the number of high frequency pulses according to the present disclosure. The exemplary time duration of On time and Off time pairs are provided with the corresponding number of the high frequency pulses.

According to the present disclosure, sufficient cosmetic improvement of the skin can be obtained without skin damage through the selection and adjustment by the adjustment unit 113, and thus safety of the high frequency (RF) application to the skin can be enhanced.

In addition, the high-frequency waveform output unit 113g may be programmed to automatically make the Off time longer than the On time when the selected number of high frequency pulses applied to the skin is increased and the adjustment by the high frequency output time adjusting unit 113a and the high frequency pulse number adjusting unit 113b.

As a result, the time for outputting high frequency (RF) may be increased in a safer manner, so that the high frequency may be evenly delivered into the skin layer for a long time and safety of the high frequency (RF) application to the skin can be enhanced.

Here, according to an embodiment of the present disclosure, when the number of pulses of high-frequency pulses moves from "5" to "6", the Off time can be automatically set to be longer than the On time, for example. However, the present disclosure is not limited thereto because modifications or changes, such as lowering the reference point to "5" or lower, may be possible.

In addition, when the number of pulses is selected in the range of 2 to N (N is a natural number), excluding 1 pulse, the high-frequency waveform output unit 113g may determine the time period of the On time and the Off time, based on the selection and the adjustment by the high frequency output time adjusting unit 113a and the high frequency pulse number adjusting unit 113b. The time period of the On time and the Off time can be determined by using Equation 1 and Equation 2.

$$\text{On time} = [T_{RF\ Time} \times \{(10 - \text{Pulse} + 1) \times 10\} \div 100] \div \text{Pulse} \quad \text{(Equation 1)}$$

$$\text{Off time} = [T_{RF\ Time} \times \{(\text{Pulse} - 1) \times 10\} \div 100] \div \text{Pulse} \quad \text{(Equation 2)}$$

Here, the $T_{RF\ Time}$ denotes the time for outputting high frequency (RF), and the Pulse denotes the number (natural number) of high frequency pulses.

That is, in order to generate high-frequency pulses and apply them to the skin for skin care or treatment of the skin according to the present disclosure, the time duration for outputting high frequency (RF) to be applied to the skin may be selected and adjusted. In the present disclosure, the number of pulses to be generated during the time for outputting the high frequency (RF) can be selected from 1 to N (N is a natural number), and if any number of 2 to N (N is a natural number), excluding 1, is selected, the On time period where pulse waveform is output and the Off time period where no pulse waveform is output is determined. If a user selects a number, higher than 1, for the number of pulse, during the time for outputting the high frequency (RF), the On time and the Off time may be output alternately and repeatedly, so that a desired high-frequency pulse may be applied to the skin during the On time period.

As a result, as described above, the time for outputting high frequency (RF) may be increased in a safer manner, so that the high frequency may be evenly delivered into the skin layer for a long time and safety of the high frequency (RF) application to the skin can be enhanced. Accordingly, the problems of the conventional method, i.e., the problems due to artificial increment of the time for outputting high frequency (total RF time) may be solved.

In addition, according to the present disclosure, it may be possible to resolve the problems of the conventional method of outputting high frequency waves and applying them to the skin: excessive coagulation of tissue in the skin, a patient feeling pain due to prolonged exposure to high frequency, skin fatigue, or side effects on the skin due to excessive treatment.

Figure 4:
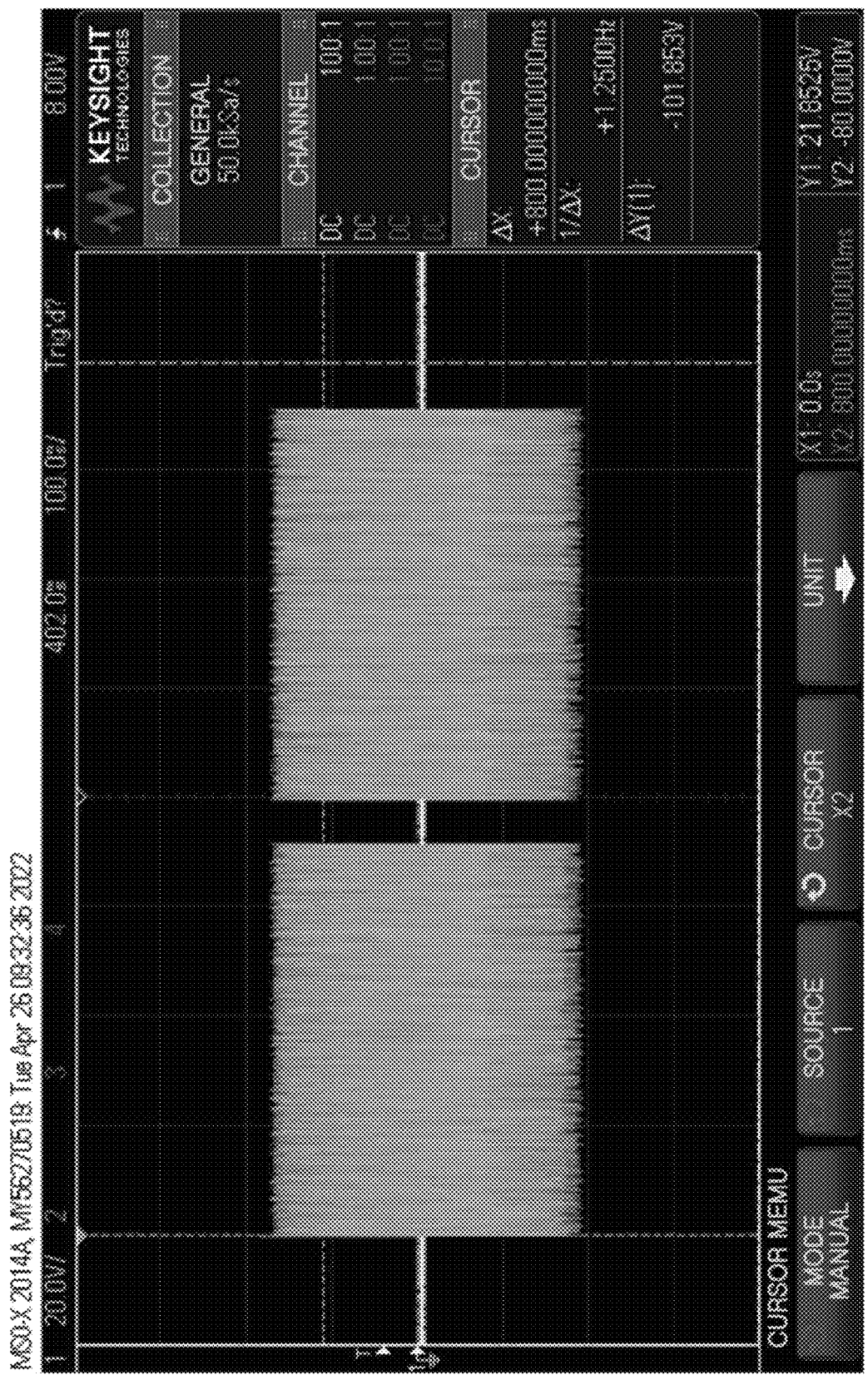
FIG. 4 shows a waveform diagram displaying an output of high-frequency pulses applied to the skin when the 2-pulse option is selected according to the present disclosure.
Figure 5:
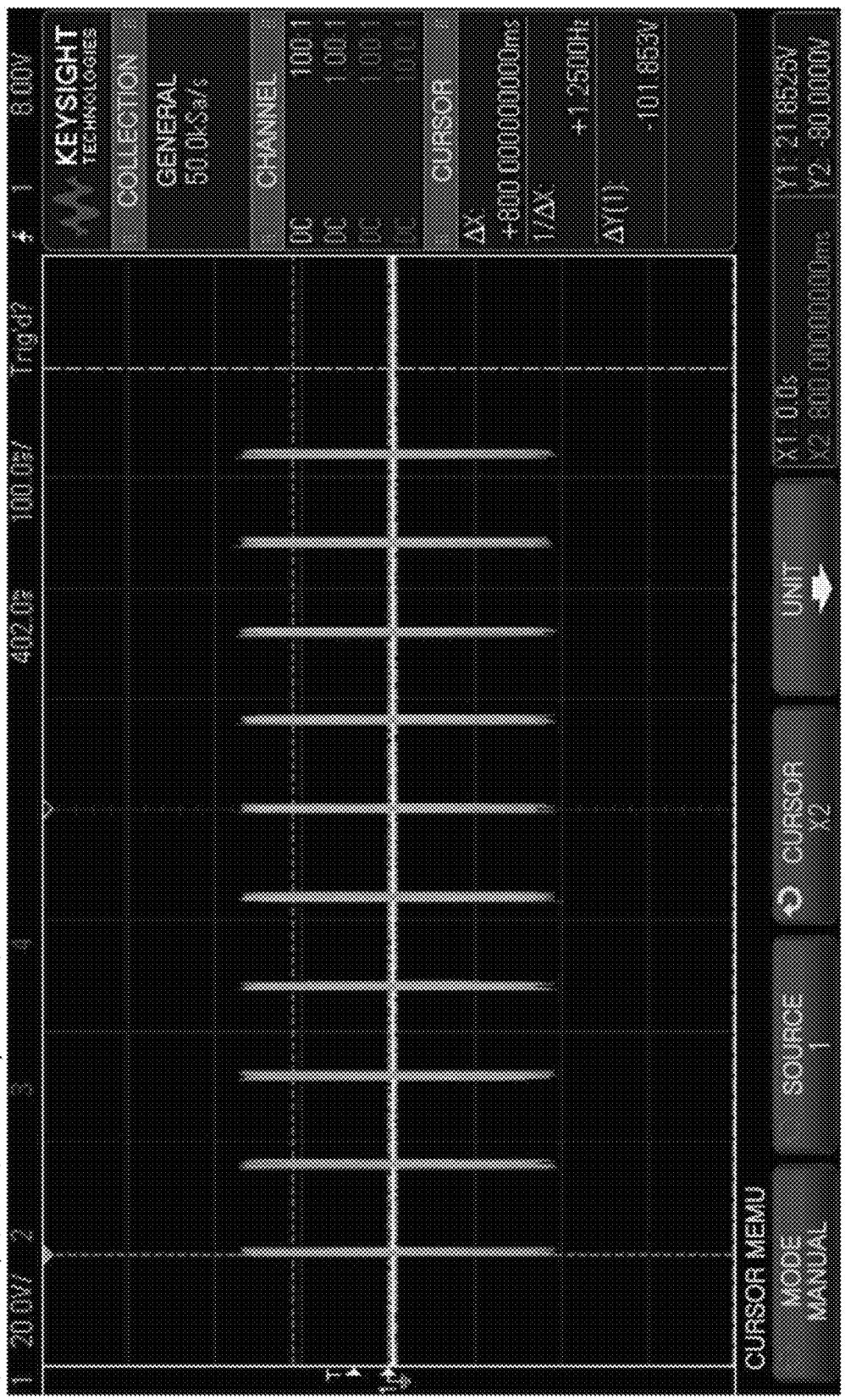
FIG. 5 shows a waveform diagram displaying an output of high-frequency pulses applied to the skin when the 10-pulse option is selected according to the present disclosure.

In addition, FIGS. 4 and 5 are waveform diagrams showing actual high-frequency waveform output by the high-frequency waveform output unit 113g based on the adjustment by the high-frequency output time adjusting unit 113a and the high-frequency pulse number adjusting unit 113b according to the present disclosure. FIG. 4 shows a waveform diagram of actual high-frequency pulses applied to the skin when the 2-pulse option is selected, and FIG. 5 shows a waveform diagram of actual high-frequency pulses applied to the skin when the 10-pulse option is selected.

Meanwhile, a specific embodiment of a method of applying a high-frequency pulse to the skin for cosmetic improvement of the skin and a device for skin care using the same according to the present disclosure can be described as follows.

Figure 1:
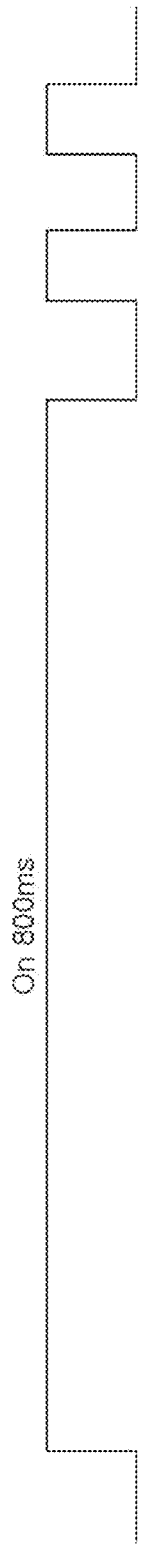
FIG. 1 shows an example of a pulse application by a conventional device for skin care using high frequency.
Figure 2:
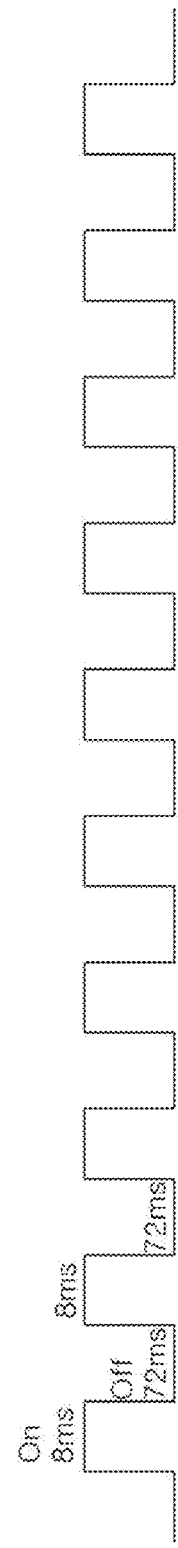
FIG. 2 shows an example of a method of applying a high-frequency pulse to the skin for skin care according to the present disclosure.

FIG. 2 shows an embodiment of the present disclosure where 10 high frequency pulses are applied during the total time for outputting high frequency of 800 ms and the On time of the high frequency pulse is adjusted to 8 ms and the Off time of the high frequency pulse is adjusted to 72 ms.

Figure 3:
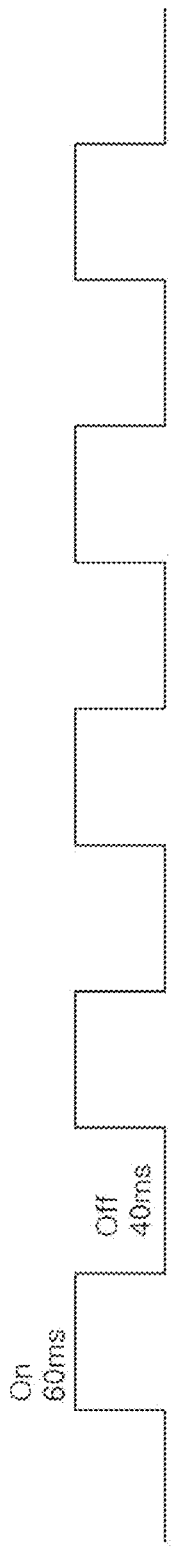
FIG. 3 shows another example of a method of applying a high-frequency pulse to the skin for skin care according to the present disclosure.

FIG. 3 shows an embodiment of the present disclosure where five high frequency pulses are applied during the total time for outputting high frequency of 500 ms and the On time of the high frequency pulse is adjusted to 60 ms and the Off time of the high frequency pulse is adjusted to 40 ms.

As such, according to the present disclosure, if a user simply adjusts the On time and the Off time of the pulse, a high-frequency pulse is divided, so it may be possible for a user to easily and precisely set high-frequency energy to be delivered to the skin. Moreover, the user may simply select the number of pulses applied during the time for outputting high frequency for adjusting the On time and the Off time of the pulse, instead of entering or selecting the On time and the Off time of the pulse.

In particular, according to the present disclosure, it was confirmed experimentally that, when 10 is selected as the number of pluses applied during the total time for outputting high frequency of 800 ms and the On time of the pulse is 8 ms and the Off time of the pulse is 72 ms, significant effects were achieved in removal of hair of various colors, including white.

In addition, as described above, it may be possible to reduce the total amount of energy applied to the skin by adjusting the method of pulses, such that the aspects of coagulative necrosis reaction, non-necrotic coagulation reaction, and non-necrotic thermal reaction can be controlled.

Here, the embodiment shown in FIG. 2, etc. is representative of embodiments where the Off time is automatically set as being longer than the On time when the selected number of high frequency pulses applied to the skin is increased, and shows that the time for outputting high frequency (RF) (Total RF time) may be increased in a safer manner so that high frequency energy may be delivered evenly into the skin layer for a long time and safety of the high frequency (RF) application to the skin can be enhanced.

Furthermore, it was seen that, when the number of pulses during the time for outputting high frequency is increased and the Off time is set as being longer than the On time, a more significant effect in cosmetic improvement of the skin was obtained.

The handpiece 120 may include an electrode unit that receives a signal of a high-frequency pulse generated by the high-frequency signal generator 112 mounted on the main body 110 and applies it to the skin.

The electrode unit of the handpiece 120 may include a plurality of electrodes.

The plurality of electrodes may include needles.

In addition, several different types of the handpiece 120 may be connected to the main body 110 and used interchangeably.

In this case, information on the type of the handpiece may be input by the user through the adjustment unit 113 mounted on the main body 110.

Meanwhile, FIGS. 10A to 12E are photographs of the epidermis and the dermis of the skin showing tissue changes when a selected number of high frequency pulses are applied to the skin during the set time for outputting high frequency according to the present disclosure.

FIGS. 10A to 10E show how tissue in the skin changes during the time for outputting high frequency of 800 ms when high-frequency pulses are applied to the control group for various options regarding the number of pulses.

Figure 10A:
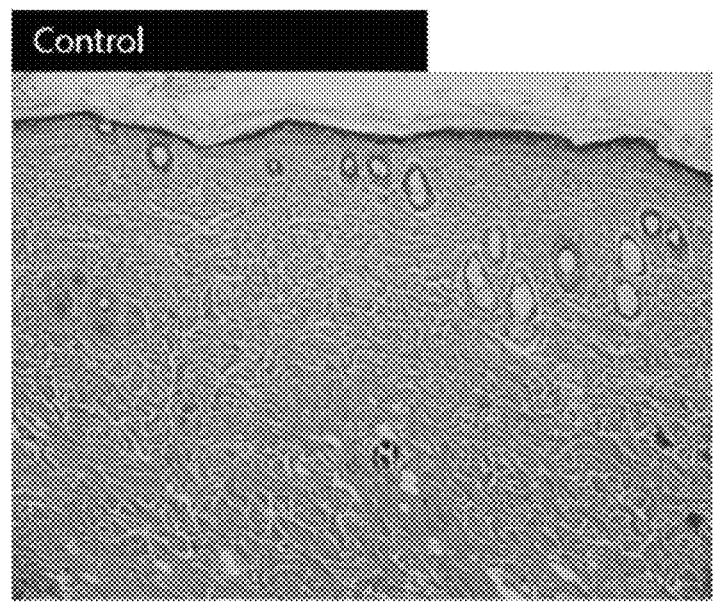
FIGS. 10A to 12E are photographs showing changes in tissue state when a selected number of high frequency pulses are applied to the skin according to the present disclosure.

FIG. 10A shows tissue in the skin of the control group to which no high-frequency pulse was applied, showing that the skin tissue overall has a purple color.

Figure 10B:
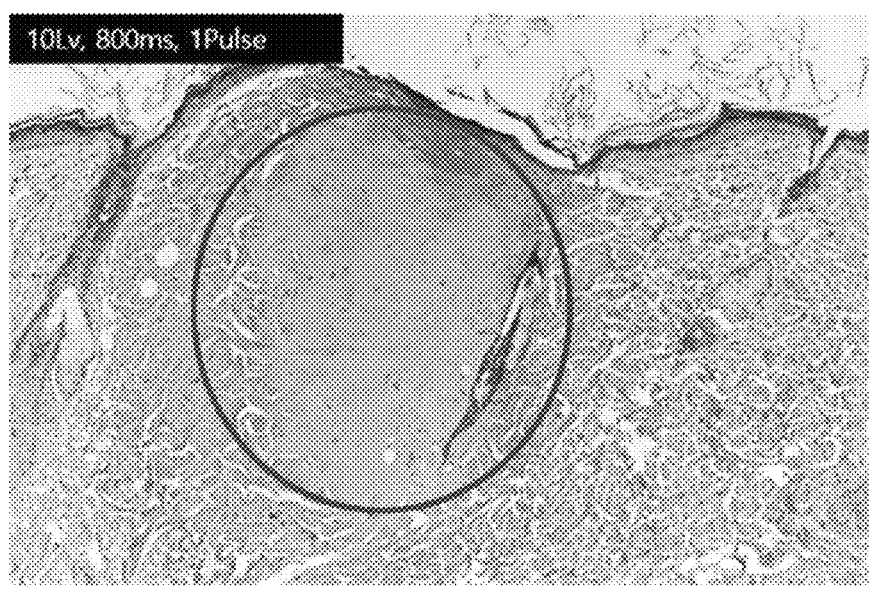

FIG. 10B shows tissue in the skin to which a high frequency of 10 Lv was applied for 800 ms under the conditions of 1-pulse option, and shows that the tissue in the skin (specifically, the tissue in the multi-depth area within the dermal layer) is coagulated as indicated in the red circle.

Figure 10C:
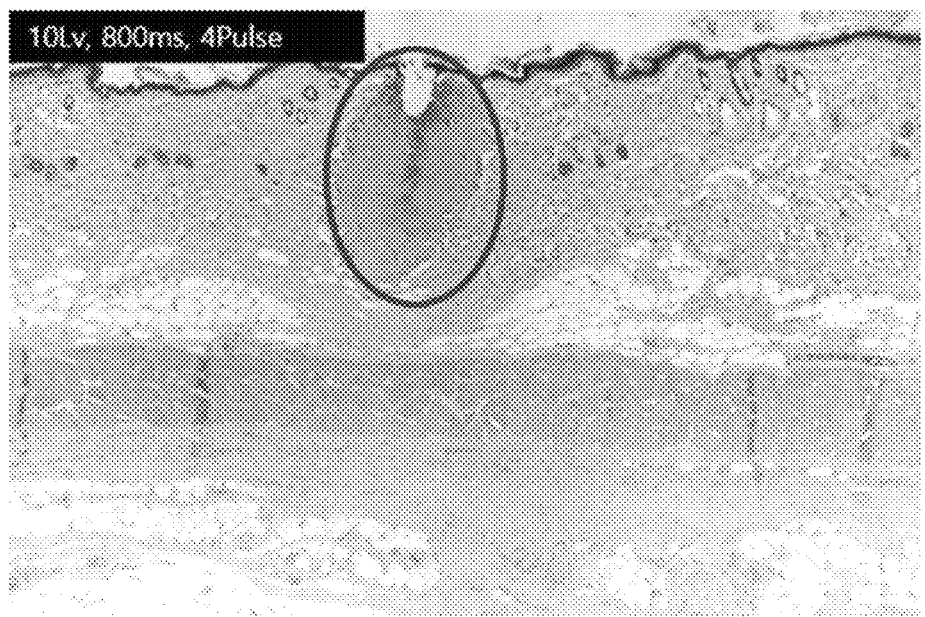

FIG. 10C shows tissue in the skin to which a high frequency of 10 Lv was applied for 800 ms under the conditions of 4 pulse option, and shows that the coagulated area in the tissue in the skin (specifically, in the tissue in the multi-depth area within the dermal layer) is smaller than that shown in FIG. 10B as indicated in the red circle. Further, it also shows that regeneration and activation of the skin (collagen) in the upper and lower layers of the tissue in the skin have begun.

Figure 10D:
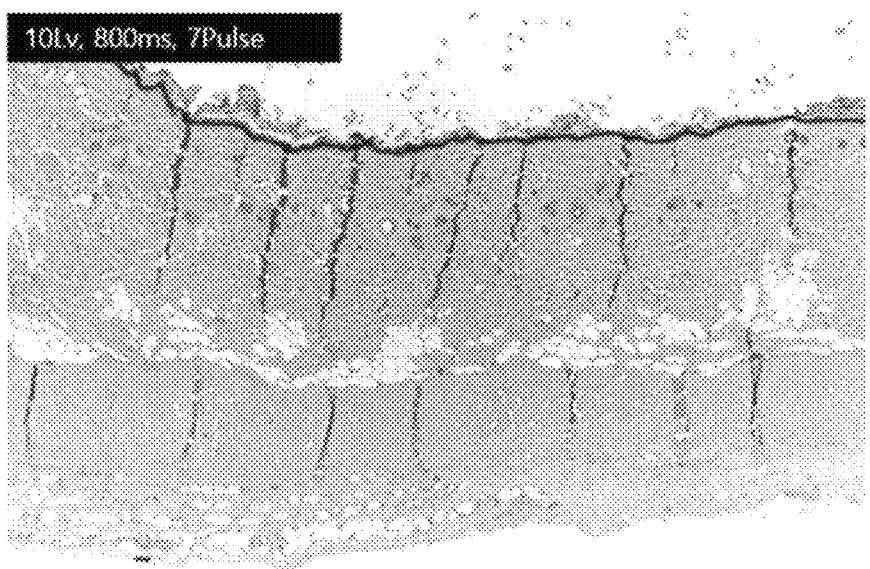

FIG. 10D shows tissue in the skin to which a high frequency of 10 Lv was applied for 800 ms under the conditions of 7-pulse option, and shows that the coagulated area in the tissue in the skin (specifically, the tissue in the multi-depth area within the dermal layer) has disappeared and regeneration and activation of the skin (collagen) in the upper and lower layers of the tissue in the skin have occurred more actively compared to in FIG. 10C.

Figure 10E:
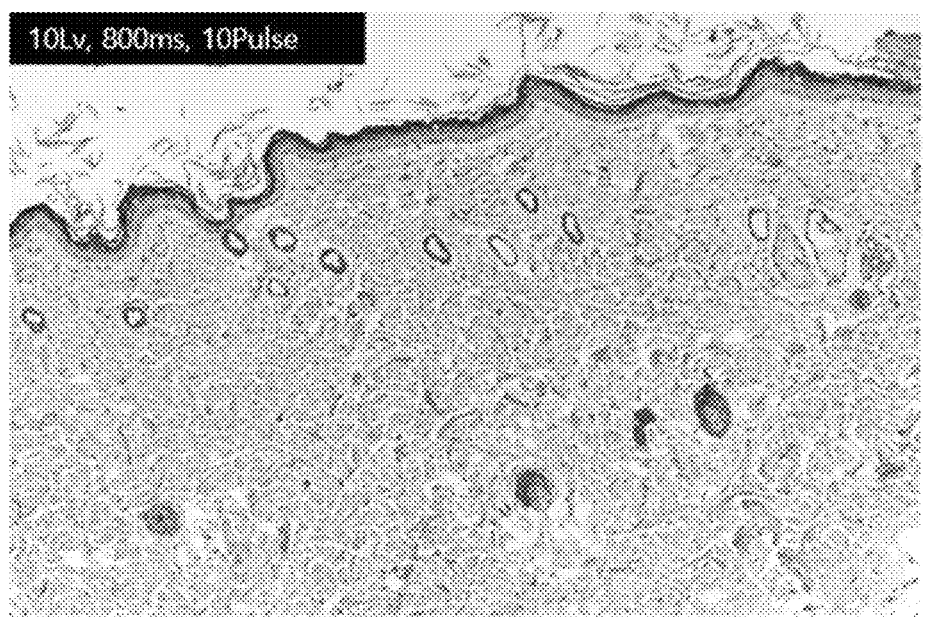

FIG. 10E shows tissue in the skin to which a high frequency of 10 Lv was applied for 800 ms under the conditions of 10-pulse option, and shows that there is no coagulated area in the tissue in the skin (specifically, the tissue in the multi-depth area within the dermal layer). In addition, it is seen that regeneration and activation of the skin (collagen) in the tissue in the skin have occurred more actively compared to in FIG. 10D and as the distinction between the upper and lower layers of the tissue has disappeared, the overall condition of the skin became stable.

In addition, FIGS. 11A to 11E are photographs showing how tissue in the skin changes during the time for outputting high frequency of 600 ms when high-frequency pulses are applied to the control group for various options regarding the number of pulses.

Figure 11A:
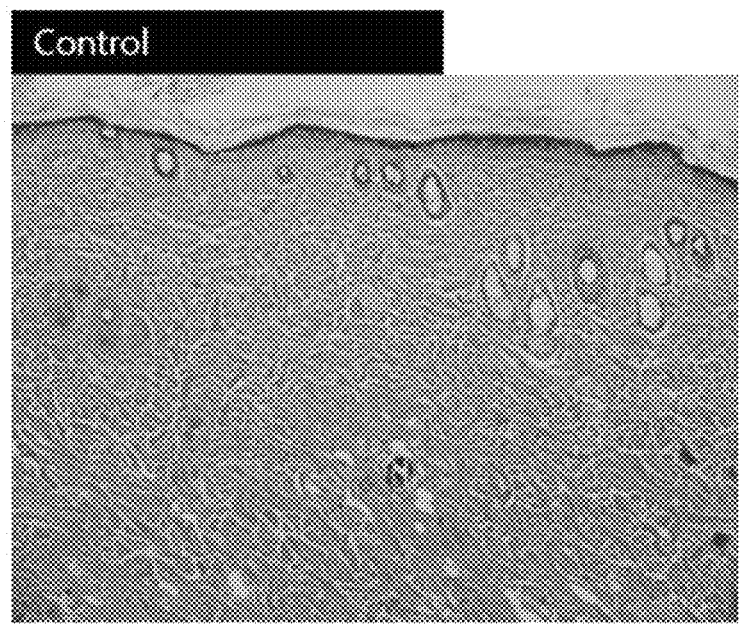

FIG. 11A shows tissue in the skin of the control group to which no high-frequency pulse was applied, showing that the skin tissue overall has a purple color.

Figure 11B:
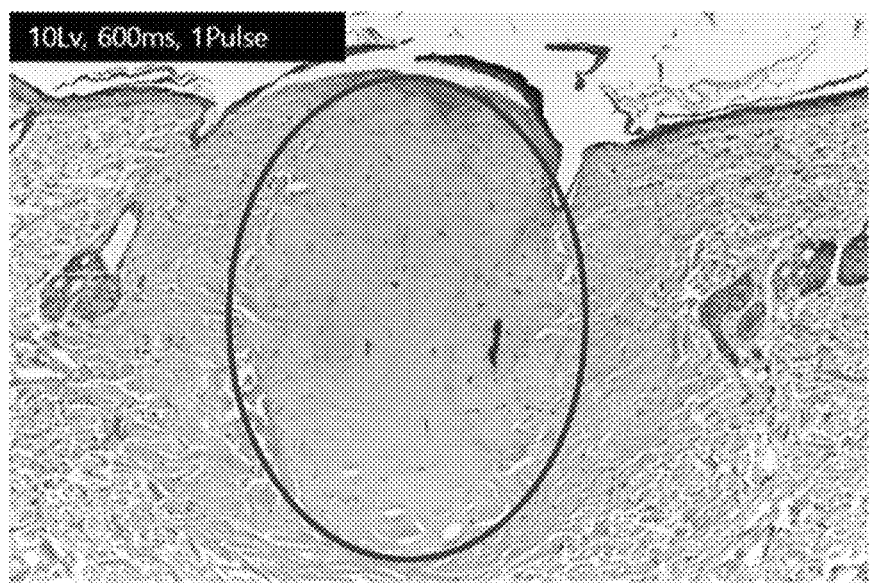

FIG. 11B shows tissue in the skin to which a high frequency of 10 Lv was applied for 600 ms under the conditions of 1-pulse option, and shows that the tissue in the skin (specifically, the tissue in the multi-depth area within the dermal layer) is coagulated as shown in the red circle.

Figure 11C:
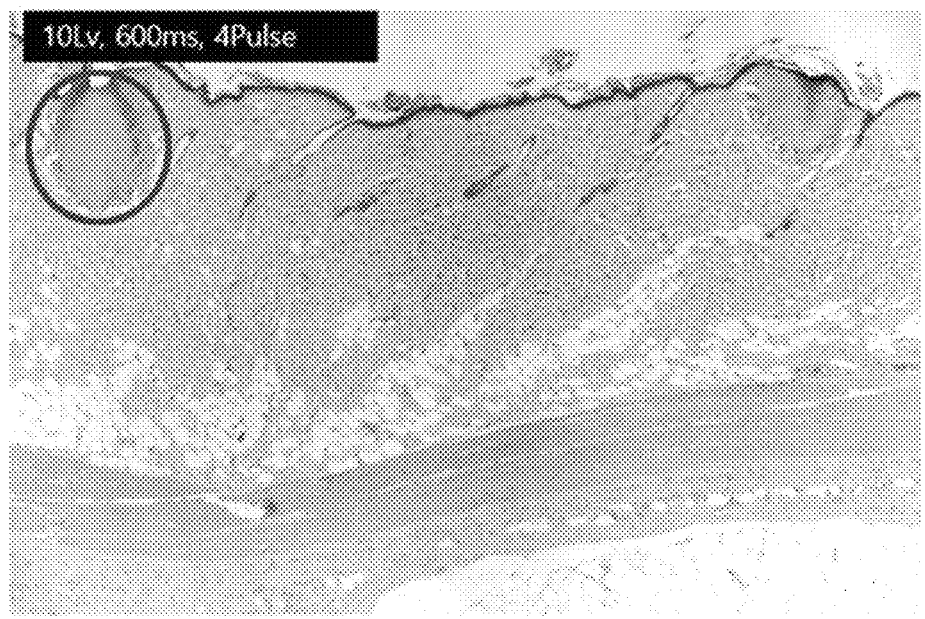

FIG. 11C shows tissue in the skin to which a high frequency of 10 Lv was applied for 600 ms under the conditions of 4-pulse option, and shows that the coagulated area in the tissue in the skin (specifically, the tissue in the multi-depth area within the dermal layer) is smaller than that in FIG. 11B as indicated in the red circle. Further, it also shows that regeneration and activation of the skin (collagen) in the upper and lower layers of the tissue in the skin have begun.

Figure 11D:
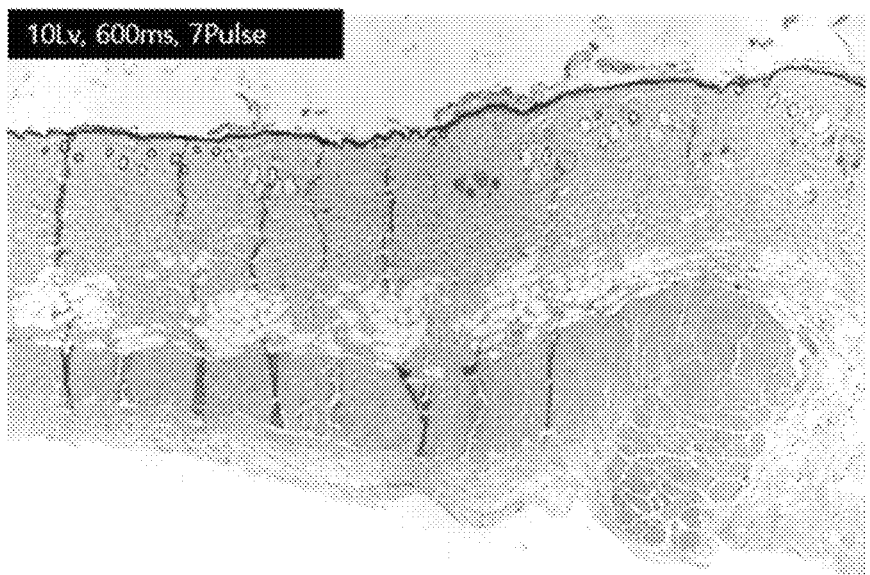

FIG. 11D shows tissue in the skin to which a high frequency of 10 Lv was applied for 600 ms under the conditions of 7-pulse option, and shows that the coagulated area in the tissue in the skin (specifically, the tissue in the multi-depth area within the dermal layer) has been further reduced and regeneration and activation of the skin (collagen) in the upper and lower layers of the tissue in the skin have occurred more actively compared to in FIG. 11C.

Figure 11E:
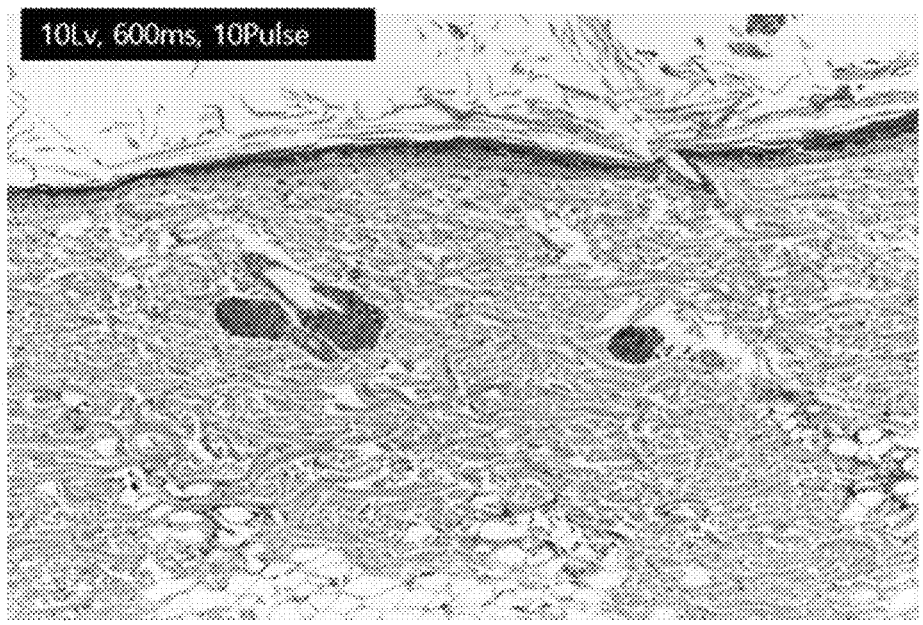

FIG. 11E shows tissue in the skin to which a high frequency of 10 Lv was applied for 600 ms under the conditions of 10-pulse option, and shows that there is no coagulated area in the tissue in the skin (specifically, the tissue in the multi-depth area within the dermal layer). In addition, it is seen that regeneration and activation of the skin (collagen) in the tissue in the skin have occurred more actively compared to in FIG. 11D. As the distinction between the upper and lower layers of the tissue has disappeared, the overall condition of the skin became stable.

In addition, FIGS. 12A to 12E show how tissue in the skin changes during the time for outputting high frequency of 400 ms when high-frequency pulses are applied to the control group for various options regarding the number of pulses.

Figure 12A:
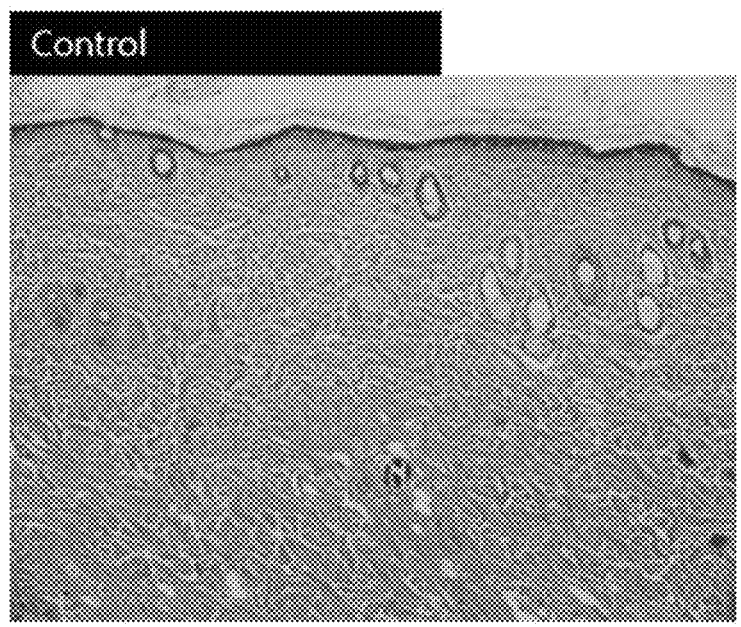

FIG. 12A shows tissue in the skin of the control group to which no high-frequency pulse was applied, showing that the skin tissue overall has a purple color.

Figure 12B:

FIG. 12B shows tissue in the skin to which a high frequency of 10 Lv was applied for 400 ms under the conditions of 1-pulse option, and shows that the tissue in the skin (specifically, the tissue in the multi-depth area within the dermal layer) is coagulated as shown in the red circle.

Figure 12C:
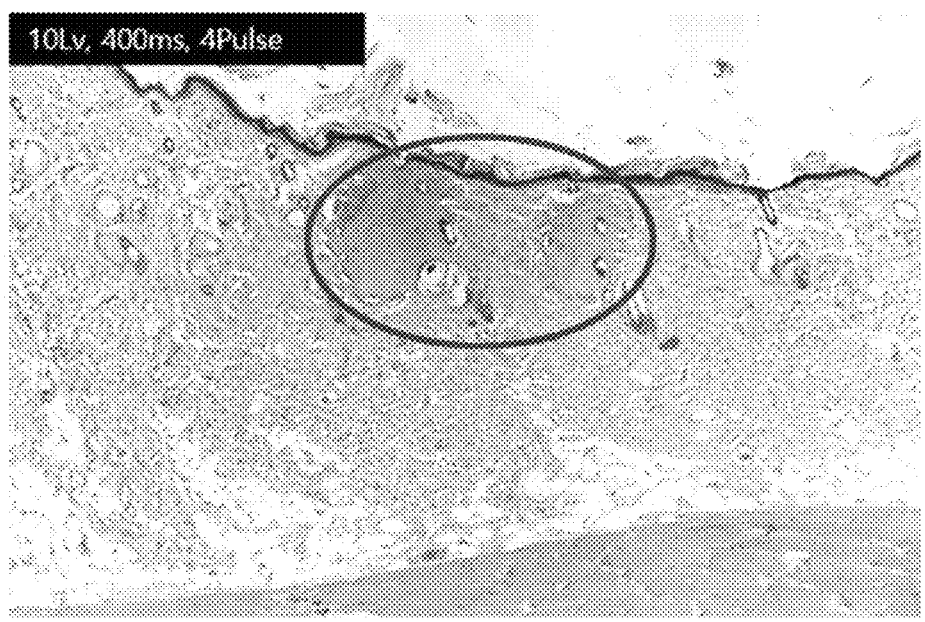

FIG. 12C shows tissue in the skin to which a high frequency of 10 Lv was applied for 400 ms under the conditions of 4-pulse option, and shows that the coagulated area in the tissue in the skin (specifically, the tissue in the multi-depth area within the dermal layer) is smaller than that in FIG. 11B as shown in the red circle and regeneration and activation of the skin (collagen) in the upper and lower layers of the tissue in the skin have begun.

Figure 12D:
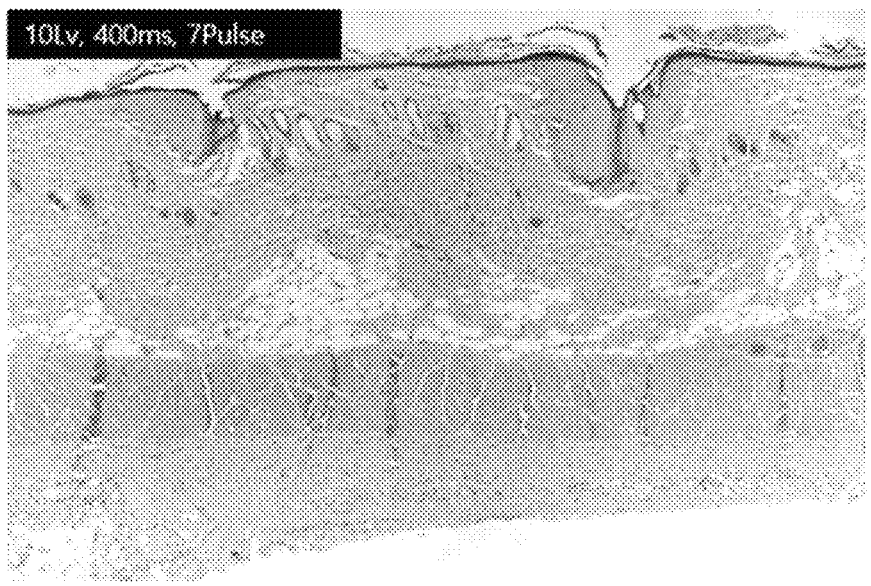

FIG. 12D shows tissue in the skin to which a high frequency of 10 Lv was applied for 400 ms under the conditions of 7-pulse option, and shows that the coagulated area in the tissue in the skin (specifically, the tissue in the multi-depth area within the dermal layer) has been further reduced and regeneration and activation of the skin (collagen) in the upper and lower layers of the tissue in the skin have occurred more actively compared to in FIG. 12C.

Figure 12E:
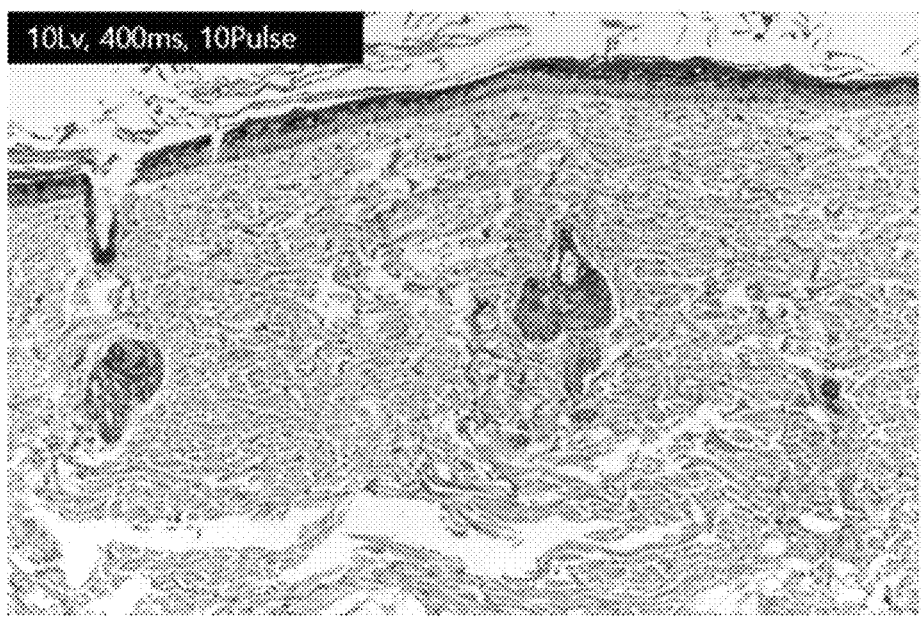

FIG. 12E shows tissue in the skin to which a high frequency of 10 Lv was applied for 400 ms under the conditions of 10-pulse option, and shows that there is no coagulated area in the tissue in the skin (specifically, the tissue in the multi-depth area within the dermal layer). In addition, it is seen that regeneration and activation of the skin (collagen) in the tissue in the skin have occurred more actively compared to in FIG. 12D. As the distinction between the upper and lower layers of the tissue has disappeared, the overall condition of the skin became stable.

That is, as shown in FIGS. 10A to 12E, according to the present disclosure, when the number of high-frequency pulses is increased, regeneration and activation of the skin (collagen) may become gradually more active, and more remarkable effects on skin care may be observed.

Accordingly, according to the present disclosure providing an improved method of applying high frequencies to the skin with the above-described features, it may be possible to carefully control the cycle and the energy of high-frequency pulses applied to the skin based on the purpose of skin care or skin treatment as well as the conditions of the skin and allow a user to arbitrarily control high frequency pulses applied to the skin.

Particularly, when the number of high-frequency pulses applied to the skin is increased, the Off time is automatically set longer than the On time when the selected number of high frequency pulses applied to the skin is increased. As a result, the time for outputting high frequency (RF) (Total RF time) may be increased in a safer manner so that it may be possible to deliver high frequency evenly into the skin layer for a relatively long time and improve safety in applying the high frequency (RF) to the skin.

In addition, it may be possible to resolve the problems of the conventional method of applying high frequency waves to the skin: excessive coagulation of tissue in the skin, a patient feeling pain due to prolonged exposure to high frequency, skin fatigue, side effects on the skin due to excessive treatment, etc.

Furthermore, according to the present disclosure, it may be possible to stably apply high-frequency pulses to the entire skin layer from the shallow layer to the deep layer and deliver them evenly into tissue in the skin, thereby enhancing the effect on skin care. In addition, it may be possible to control the aspects of the skin's coagulative necrotic reaction, non-necrotic coagulation reaction, and non-necrotic thermal reaction by using the enhanced method of applying high-frequency pulses to the skin. The cosmetic improvement of the skin, including removal of hair of various colors is also expected.

The embodiments described above are only desirable embodiments of the present disclosure, and the present disclosure is not limited to these embodiments. Furthermore, various modifications, variations, substitutions, etc. can be made by a person having ordinary skill in the art within the scope of the technology and the claims of the present disclosure, and they should fall within the scope of the technical rights of the present disclosure.

The invention claimed is:

1. A skin care method based on high-frequency pulses application, comprising:
   generating the high-frequency pulses and applying the high-frequency pulses to the skin,
   wherein said generating and applying the high-frequency pulses includes outputting high frequency (RF) for a certain period of time to the skin,
   wherein the high frequency (RF) output for the certain period of time has a selected number of pulses in the range of 2 to N (N is a natural number less than 11),
   wherein each pulse has On time and Off time, the On time is a time period when pulse waveform is output, and the Off time is a time period when no pulse waveform is output,
   wherein the On time and the Off time are alternately repeated based on the number of pulses during the certain period of time for outputting high frequency (RF), so that a desired high-frequency pulse is applied to the skin during the On time, and
   wherein when the selected number of pulses is any one of 2 to N, the time period of the On time is determined by Equation 1 and the time period of the Off time is determined by Equation 2; whereby $$\text{On time} = [TRF\ Time \times \{(10-\text{Pulse}+1) \times 10\} \div 100] \div \text{Pulse} \quad \text{(Equation 1)}$$

$$\text{Off time} = [TRF\ Time \times \{(\text{Pulse}-1) \times 10\} \div 100] \div \text{Pulse}, \quad \text{(Equation 2)}$$

wherein the TRF Time denotes the certain period of time for outputting high frequency (RF), and the Pulse denotes the selected number (natural number) of high frequency pulses.

2. The method of claim 1,
   wherein the certain period of time for outputting high frequency (RF) is in the range of 100 ms to 7,000 ms,
   wherein a frequency of the high frequency (RF) is in the range of 0.5 MHz to 2 MHz, and
   wherein energy of the high frequency (RF) is in the range of 0.0025 J to 192 J.

3. The method of claim 1,
   wherein when the selected number of high frequency pulses applied to the skin is greater than a preset number, the Off time is set longer than the On time so that the time for outputting high frequency (RF) is increased in a safer manner, thereby delivering high frequency evenly into the skin for a relatively long time and improving safety in the high frequency application to the skin.

4. The method of claim 1,
   wherein the time period for outputting the high frequency (RF), the frequency of the high frequency and the energy of the high frequency are respectively adjustable.

5. A device for skin care that generates high-frequency pulses and applies them to the skin, comprising:
   a main body; and
   a handpiece connected to the main body to apply high-frequency pulses to the skin,
   wherein the main body includes:
   a power supply unit for supplying power to the device;
   a high-frequency signal generator for generating a high-frequency signal to be applied to the skin;
   an adjustment unit for determining an adjustment of an output of high frequency signal generator; and
   a controller for controlling an operation of the device and the output of high-frequency pulses in response to the adjustment determined by the adjustment unit,
   the adjustment unit includes:
   a high frequency output time adjusting unit for determining an adjustment of a time period for outputting high frequency (RF) to be applied to the skin;
   a high frequency (RF) pulse number adjusting unit for determining an adjustment of the number of pulses in the range of 2 to N (N is a natural number less than 11),
   a high frequency output intensity adjusting unit for determining an adjustment of the intensity of the output of high-frequency (RF);

a high-frequency frequency adjusting unit for determining an adjustment of a high-frequency (RF) frequency;

a high frequency pulse width adjusting unit for determining an adjustment of the width of a high frequency (RF) pulse;

a needle length adjusting unit for determining an adjustment of a length of a needle to be inserted into the skin, the needle being mounted on the handpiece; and a high-frequency waveform output unit for determining a pulse waveform according to the adjustment determined by the high frequency output time adjusting unit and the high frequency pulse number adjusting unit, wherein each pulse of the pulse waveform has On time and Off time, the On time is a time period when pulse waveform is output, and the Off time is a time period when no pulse waveform is output;

wherein when the selected number of pulses is any one of 2 to N, the On time and the Off time are alternately repeated based on the number of pulses during the time period for outputting high frequency (RF), so that a desired high-frequency pulse is applied to the skin during the On time, and wherein when the selected number of pulses is any one of 2 to N, the time period of the On time is determined by Equation 1 and the time period of the Off time is determined by Equation 2; whereby On time=[$TRF$ Time×{(10−Pulse+1)×10}÷100]÷Pulse  (Equation 1)

Off time=[$TRF$ Time×{(Pulse−1)×10}÷100]÷Pulse,  (Equation 2)

wherein the TRF Time denotes the time period for outputting high frequency (RF), and the Pulse denotes the selected number of high frequency pulses.

6. The device for skin care of claim 5, wherein the handpiece includes an electrode unit that receives a high-frequency pulse signal generated by the high-frequency signal generator and applies it to the skin.

7. The device for skin care of claim 6, wherein the electrode unit includes a plurality of electrodes.

8. The device for skin care of claim 7, wherein the plurality of electrodes include needles.

9. The device for skin care of claim 5,
wherein the time period for outputting high frequency (RF) is in the range of 100 ms to 7,000 ms,
wherein the frequency of the high frequency (RF) is in the range of 0.5 MHz to 2 MHz, and
wherein the energy of the high frequency (RF) is in the range of 0.0025 J to 192 J.

10. The device for skin care of claim 5, wherein the high-frequency waveform output unit is configured to set the Off time longer than the On time when the selected number of high frequency pulses applied to the skin is greater than a preset number, so that the time for outputting high frequency (RF) is increased in a safer manner, thereby delivering high frequency evenly into the skin for a relatively long time and improving safety in the high frequency application to the skin.

11. The device for skin care of claim 5, wherein the time period for the On time and the Off time is adjustable by using the adjustment unit.

12. The device for skin care of claim 5, wherein a plurality of types of handpieces are attachable to the main body and they can be interchanged with each other, and wherein a type of the handpiece to be used can be designated by using the adjustment unit.

\* \* \* \* \*